United States Patent [19]

Brown

[11] 4,300,203
[45] Nov. 10, 1981

[54] METHOD AND MEANS FOR OPERATING LOGARITHMIC CIRCUITS

[75] Inventor: James R. Brown, Garden Grove, Calif.

[73] Assignee: Beckman Instruments, Inc., Fullerton, Calif.

[21] Appl. No.: 86,387

[22] Filed: Oct. 19, 1979

[51] Int. Cl.³ .............................................. G06F 7/02
[52] U.S. Cl. .................................. 364/577; 364/498; 364/570; 356/325
[58] Field of Search ................ 364/577, 570, 497–499, 364/857; 356/319–325

[56] References Cited

U.S. PATENT DOCUMENTS

| | | | |
|---|---|---|---|
| 3,633,012 | 1/1972 | Wilhelmson et al. | 364/857 X |
| 3,720,813 | 3/1973 | Badessa | 364/577 X |
| 4,063,816 | 12/1977 | Itoi et al. | 356/325 X |
| 4,092,069 | 5/1978 | Fukuda et al. | 356/325 |
| 4,093,991 | 6/1978 | Christie, Jr. et al. | 364/498 X |
| 4,171,913 | 10/1979 | Wildy et al. | 364/498 X |

Primary Examiner—Edward J. Wise
Attorney, Agent, or Firm—R. J. Steinmeyer; Robert R. Meads

[57] ABSTRACT

A method and means for operating log converter circuits in which the method comprises the steps of sequentially conducting to the input of the log converter circuit signals representing a known transmittance (T) of 100% T, 10% T, 1% T, and 0.1% T, these signals covering the range of operation of the log converter circuit, storing the outputs of the circuit as signals representing an absorbance (A) of 0A, 1A, 2A, and 3A, respectively, conducting to the input of the log converter circuit an unknown signal, and utilizing a microcomputer to perform a linear interpolation of the output of the circuit with the unknown signal applied thereto using the previously stored 0A, 1A, 2A, and 3A signals.

18 Claims, 2 Drawing Figures

METHOD AND MEANS FOR OPERATING LOGARITHMIC CIRCUITS

BACKGROUND OF THE INVENTION

1. Field of the Invention

The present invention relates to a method and means for operating logarithmic circuits and, more particularly, to a method and apparatus for calibrating logarithmic circuits by storing known absorbance signals and subsequently determining the value of an unknown absorbance signal by comparison with the stored signals.

2. Description of the Prior Art

A variety of different types of instruments use log converter circuits for providing an output which is the log of the input or the reciprocal of the input. A spectrophotometer is an example of such an instrument. In a spectrophotometer, a beam of light of a known frequency is transmitted through a sample and a photomultiplier tube is positioned to detect the light passing through the sample. The less light absorbed by the sample, the more light is transmitted and the output of the photomultiplier tube is a current signal proportional to the intensity of the received light. Thus, the output of the photomultiplier tube is proportional to transmittance.

An operational amplifier is typically used to convert this current signal into a voltage signal and many circuits operate directly on this voltage signal, where transmittance is the desired output. On the other hand, spectrophotometers usually present sample light absorbance/transmittance data in units of absorbance (A) defined generally as:

$$A = \log(1/T) \quad (1)$$

where T is the fraction of light transmitted through the sample under test, with respect to a blank or standard sample.

Sophisticated instruments must concern themselves with two problems when using a photomultiplier tube and a log converter circuit, such as in a spectrophotometer. That is, it is desired that the relationship between absorbance and transmittance be exactly logarithmic and that a 100% transmittance signal correspond exactly to 0.0 absorbance signal. However, in practice, the output of a log converter circuit is rarely exactly 0.0A when the output of the photomultiplier tube is 100%T and it is difficult and expensive to construct highly accurate log converters which will provide an exactly logarithmic relationship between absorbance and transmittance.

In the past, it has generally been necessary to use expensive log converters and it is still usually necessary to require numerous electronic adjustments to tailor the output in a logarithmic fashion. The overall cost of a sophisticated instrument such as a spectrophotometer could be significantly reduced if there was a low cost, minimal calibration, analog log converter available. However, log converters meeting this requirement and still performing in a satisfactory manner have been unavailable heretofore.

SUMMARY OF THE INVENTION

The present invention satisfies the need for a low cost, minimal calibration, analog log converter for use in spectrophotometers and other instruments utilizing logarithmic circuits. According to the present invention, an expensive, highly accurate, log converter is not required. A low cost log converter may be utilized having an output which is approximately, but not exactly, logarithmic. Following the teachings of the present invention, the output of such a log converter may be calibrated, in a relatively simple manner, to provide data which is equivalent to that obtained using substantially more sophisticated log converters.

Briefly, the present method for calibrating a log converter circuit comprises the steps of sequentially conducting to the input of such log converter circuit signals representing a known transmittance (T) of 100%T, 10%T, 1%T, and 0.1%T, which signals cover the range of operation of the log converter circuit, storing the outputs of the circuit as signals representing an absorbance (A) of 0A, 1A, 2A, and 3A, respectively, conducting to the input of the log converter circuit an unknown signal, and performing a linear interpolation of the output of the circut with the unknown signal applied thereto using the previously stored 0A, 1A, 2A, and 3A signals. By this method, an accurate measure of absorbance may be obtained using an inexpensive log converter with uncalibrated scale factor and output offset.

OBJECTS, FEATURES, AND ADVANTAGES

It is therefore an object of the present invention to satisfy the need for a low cost, minimal calibration, analog log converter for use in spectrophotometers and other instruments requiring precision log conversion. It is a feature of the present invention to satisfy this need by the use of a relatively unsophisticated log converter which utilizes a microcomputer's ability to interpolate between reference readings. An advantage to be derived is that relatively inaccurate log converters may be used to perform precision logging functions. A further advantage is that inexpensive log converter circuits can be used to perform precision logging functions. A still further advantage is that a relatively inaccurate, inexpensive log converter circuit can be used to perform precision logging functions with minimal calibration.

Still other objects, features, and attendant advantages of the present invention will become apparent to those skilled in the art from a reading of the following detailed description of the preferred embodiment constructed in accordance therewith, taken in conjuction with the accompanying drawings wherein:

DESCRIPTION OF THE PREFERRED EMBODIMENT

Figure 1:
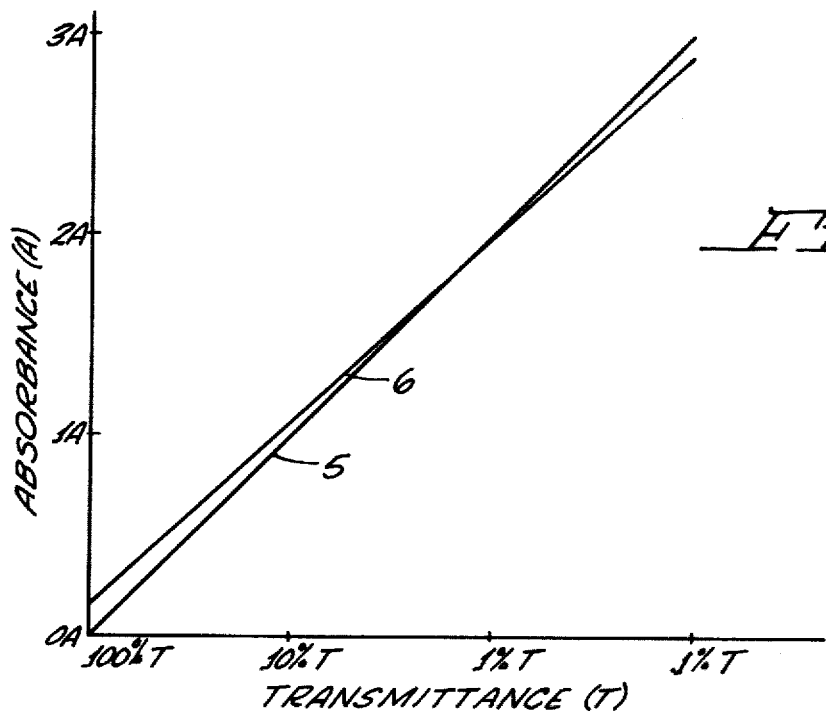
FIG. 1 is a graph showing the relationship between absorbance (A) and transmittance (T) for an ideal log converter circuit and an inexpensive log converter circuit.

Referring now to the drawings and, more particularly, to FIG. 1 thereof, there is shown first and second plots 5 and 6 on a graph of absorbance (A) as a function of transmittance (T). Plot 5 shows the output of an ideal log converter circuit where it can be seen that the relationship between absorbance and transmittance is linear on a logarithmic scale. That is, 100%T corresponds to 0.0A, 10%T corresponds to 1A, 1%T corresponds to 2A, 0.1%T corresponds to 3A, etc. Plot 6 shows the typical output of an inexpensive log converter, of the type usable according to the present invention, where it is seen that while absorbance generally follows the ideal relationship with transmittance, the relationship is not exactly linear on a logarithmic scale. In addition, 100%T does not correspond exactly to 0A.

Figure 2:
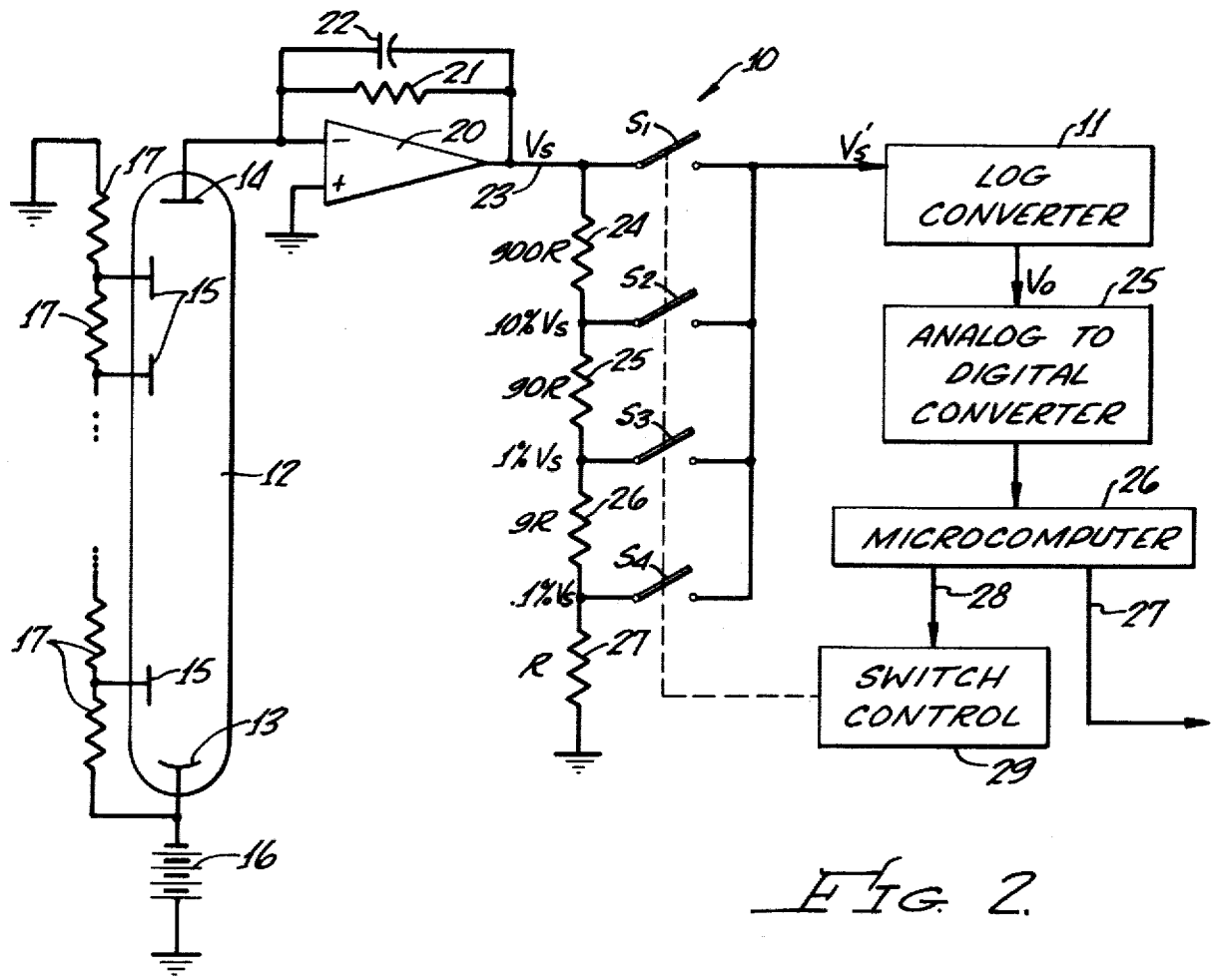
FIG. 2 is a block diagram of apparatus constructed in accordance with the teachings of the present invention.

Referring now to FIG. 2, there is shown apparatus, generally designated 10, constructed in accordance with the teachings of the present invention, which includes a low cost analog log converter 11, one having an output similar to that shown as plot 6 in FIG. 1, which can be used to perform precision logging functions. For purposes of example, log converter 11 will be described as converting the output of a photomultiplier tube 12, representing transmittance, into an output voltage representing absorbance. However, it will be obvious to those skilled in the art that log converter 11 may be used in any circuit in which logging functions are required.

Photomultiplier tube 12 may be a conventional photomultiplier tube including a cathode 13, and anode 14, and a plurality of dynodes 15. Cathode 13 is connected to one terminal of voltage source 16, the other terminal of which is connected to ground. Bias for dynodes 15 is provided by means of a plurality of resistors 17 connected in series between voltage source 16 and ground. The taps between resistors 17 are connected to dynodes 15. This is a conventional means of biasing a photomultiplier tube.

Anode 14 of photomultiplier tube 12 is connected to the inverting input of an operational amplifier 20 functioning as a preamplifier, the non-inverting input of which is connected to ground. The output of operational amplifier 20 is fed back to the inverting input thereof, typically by means of a resistor 21 and a capacitor 22. This establishes a time constant for operational amplifier 20 which is effective in filtering noise.

The output of photomultiplier tube 12 from anode 14 is a current signal which is directly proportional to the light intensity falling on tube 12. This current signal is applied to operational amplifier 20 which provides an output signal on a line 23 which is a DC signal voltage, the magnitude of which is directly proportional to light intensity.

The output of operational amplifier 20 is connected to a voltage divider network consisting of four resistors 24–27 connected in series between line 23 and ground. While the exact values of resistors 24–27 is not important, the relationship therebetween is. That is, if resistor 17 has some value R, then resistor 26 has the value 9R, resistor 25 has the value 90R, and resistor 24 has the value 900R. It is seen that the combined resistance of resistors 24–27 is exactly 1000R and that resistors 24–27 function to divide the output of operational amplifier 20 in 10% steps. Thus, if the output of operational amplifier 20 is defined as 100%$V_s$, the voltage at the junction between resistors 24 and 25 is 10%$V_s$, the voltage at the junction between resistors 25 and 26 is 1%$V_s$, and the voltage at the junction between resistors 26 and 27 is 0.1%$V_s$.

The 100%$V_s$, 10%$V_s$, 1%$V_s$, and 0.1%$V_s$ signals are applied to first ends of switches S1, S2, S3, and S4, respectively, the other ends of which are all connected to the signal input of log converter 11. This signal is defined as $V_s'$.

The output of log converter 11, which is a DC voltage, defined as $V_o$, is applied to an anolog-to-digital converter 25 which converts the analog DC output voltage to a digital signal. This signal is applied to a microcomputer 26 which may be any of the conventional types presently on the market having storage, calculation, and instruction issuing capabilities. Microcomputer 26 is capable of producing, on a line 27, an output signal indicative of absorbance as determined by log converter 11, as will be described more fully hereinafter. Microcomputer 26 is also capable of forwarding control signals via lines 28 to a switch control circuit 29 for sequentially opening and closing the individual switches S1–S4. This operation will also be described more fully hereinafter.

In operation, the function of apparatus 10 is to convert a low cost, minimal calibration, analog log converter, such as log converter 11, into one capable of performing precision logging functions. To achieve this, a suitable 100%T signal is generated in a normal fashion using a real blank sample. That is, light is directed through a blank sample onto photomultiplier tube 12 so that the output of preamplifier 20, $V_s$, is, by definition, 100%T. This signal also corresponds, by definition to a 0.0A signal. Thus, with $V_s=100\%T$, microcomputer 26 signals switch control 29 to close switch S1 so that $V_s'=V_s$ signal is conducted to the input of log converter 11. The output of log converter 11 is digitized by converter 25 and conducted to microcomputer 26 which reads and stores the resulting log converter output as a 0A signal. While the signal typically will not correspond to zero volts, it is still defined as a 0A signal.

Microcomputer 26 then signals switch control 29 to open switch S1 and close switch S2. A voltage $V_s'=0.1V_s$ is thus presented to the input of log converter 11. This voltage represents a 10%T signal so that $V_o$ represents a 1.0A signal. Microcomputer 26 reads and stores this 1A output signal after digitization by converter 25

This process is now rapidly repeated with microcomputer 26 sequentially signalling switch control 29 to close switch S3 and then switch S4, presenting the equivalent of 1%T and 0.1%T signals to log converter 11 and storing the equivalent 2A and 3A signals which result.

At this time, microcomputer 26 has stored therein numerical outputs of log converter 11 which are known to correspond to 0A, 1A, 2A, and 3A. Accordingly, switch S1 only is now closed and apparatus 10 is ready for use in making measurements of real samples. That is, a real sample under test is inserted into the spectrophotometer and the output of photomultiplier tube 12 is conducted via preamplifier 20 and switch S1 to log converter 11. Log converter 11 provides an output which is digitized by converter 25 and fed to microcomputer 26. Microcomputer 26 performs a simple linear interpolation of the signal using the previously stored 0A, 1A, 2A, and 3A signals to determine the exact absorbance value of the real sample. The output of microcomputer 26, which may be any value of absorbance between 0 and 3A, is provided on line 27 for use by the spectrophotometer.

It can therefore be seen that the present invention satisfies the need for a low cost, minimal calibration, analog log converter for use in spectrophotometers and other instruments utilizing logarithmic circuits. With the present invention, an inexpensive, highly accurate log converter is not required. A low cost log converter may be utilized having an output which is approximately, but not exactly, logarithmic. Following the teachings of the present invention, the output of such a log converter may be calibrated in a relatively simple manner, and very rapidly, to provide data which is equivalent to that obtained using substantially more sophisticated log converters.

All of the apparatus required for implementing the present method is known to those skilled in the art. Log converters and analog-to-digital converters are readily available. Microcomputer which are capable of storing input date, issuing instructions, and performing a linear interpolation are also readily available. Switch control 29 and switches S1-S4 may be mechanical or electrical elements.

While the invention has been described with respect to the preferred physical embodiment constructed in accordance therewith, it will be apparent to those skilled in the art that various modifications and improvements may be made without departing from the scope and spirit of the invention. Accordingly, it is to be understood that the invention is not to be limited by the specific illustrative embodiment, but only by the scope of the appended claims.

I claim:

1. A method for operating a log converter circuit comprising the steps of:
   sequentially conducting signals to the input of said log converter circuit, each signal representing a known transmittance of light through a sample, said signals being spaced within the range of operation of said log converter circuit;
   storing the resultant outputs of said circuit as signals representing equivalent absorbances;
   conducting to said input of said circuit an unknown signal; and
   comparing the resultant unknown output of said circuit with said unknown signal applied thereto with the stored outputsto determine the value of said unknown output.

2. A method according to claim 1, where the step of conducting to said input of said circuit signals representing a known transmittance comprises the step of:
   sequentially conducting to said input of said log converter circuit signals representing a known transmittance (T) of 100%T, 10%T, and 1%T.

3. A method according to claim 2, wherein the step of storing the resultant outputs of said circuit comprises the step of:
   storing the resultant outputs of said circuit with the input thereto representing a transmittance of 100%T, 10%T, and 1%T as signals representing a known absorbance (A) of 0A, 1A, and 2A, respectively.

4. A method according to claim 1, 2, or 3, wherein the step of comparing the unknown output of said circuit with the stored outputs comprises the step of :
   performing a linear interpolation of the unknown output of said circuit with said unknown signal applied thereto using said stored outputs.

5. A method according to claim 4, further comprising the step of:
   converting the analog output of said log converter circuit to a digital signal before storing or comparing the output thereof.

6. A method according to claim 5, wherein the step of comparing the unknown output of said circuit with the stored outputs is performed by a computer.

7. A method for operating a log converter circuit comprising the steps of:
   sequentially conducting at least two signals to the input of said log converter circuit, each of said input signals having a known value, said signals being spaced within the range of operation of said log converter circuit;
   storing the resultant outputs of said circuit as output signals having known values;
   conducting to said input of said circuit an input signal having an unknown value; and
   comparing the resultant unknown output of said circuit with said unknown signal applied thereto with the stored outputs to determine the value of said unknown output.

8. A method according to claim 7, wherein the step of conducting input signals to said input of said circuit comprises the step of:
   sequentially conducting to said input of said log converter circuit input signals having known values which differ from each other in precise franctional steps.

9. A method according to claim 7 or 8, wherein the step of comparing the unknown output of said circuit with the stored outputs comprises the step of:
   performing a linear interpolation of the unknown output of said circuit with said unknown input signal applied thereto using said stored outputs.

10. A method according to claim 9, further comprising the step of:
    converting the analog output of said log converter circuit to a digital signal before storing or comparing same.

11. A method according to claim 10, wherein the step of comparing the unknown output of said circuit with the stored outputs is performed by a computer.

12. Apparatus for operating a log converter circuit comprising:
    means for sequentially conducting at least two input signals to the input of said log converter circuit, each of said input signals having a known value, said signals being within the range of operation of said log converter circuit;
    means for storing the outputs of said circuit as output signals having known values;
    means for conducting to said input of said circuit an input signal having an unknown value; and
    means for comparing the unknown output signal of said circuit with said unknown input signal applied thereto with the stored output signals to determine the value of said unknown output signal.

13. Apparatus according to claim 12, wherein the output of said log converter circuit is an analog signal and further comprising:
    an analog-to-digital converter coupled to the output of said log converter circuit for converting the analog output thereof to a digital signal.

14. Apparatus according to claim 13, wherein said storing means comprises:
    digital signal memory means.

15. Apparatus according to claim 14, wherein said comparing means comprises:
    calculator means for performing a linear interpolation of said unknown output signal using said stored output signals.

16. Apparatus according to claim 12, 13, 14, or 15, wherein said log converter circuit is operative to convert transmittance information to absorbance information and wherein said input signals represent known values of transmittance of light through a sample.

17. Apparatus according to claim 16, wherein said output signals represent known values of absorbance.

18. Apparatus according to claim 17, wherein said input signals have known values of transmittance which differ from each other in precise fractional steps.

* * * * *